United States Patent [19]

Gerns et al.

[11] Patent Number: 5,138,076
[45] Date of Patent: Aug. 11, 1992

[54] PROCESS FOR THE PREPARATION OF 2-(2-BROMO-2-NITROETHENYL)FURAN

[75] Inventors: Fred R. Gerns; Larry D. Timberlake, both of W. Lafayette, Ind.

[73] Assignee: Great Lakes Chemical Corporation, W. Lafayette, Ind.

[21] Appl. No.: 686,427

[22] Filed: Apr. 16, 1991

Related U.S. Application Data

[63] Continuation-in-part of Ser. No. 621,339, Dec. 3, 1990, abandoned.

[51] Int. Cl.$^5$ .................................. C07D 307/40
[52] U.S. Cl. ........................................... 549/491
[58] Field of Search ................................ 549/491

[56] References Cited

U.S. PATENT DOCUMENTS 4,743,617  5/1988  Bargar et al. ............... 549/491
4,962,212  10/1990  Smith ........................ 549/491

OTHER PUBLICATIONS

*Khim. Farm. Zh.*, vol. 6 (10), pp. 629-632 (1972), Z. N. Nazarova and G. F. Potemkin.
*Zh. Org. Khim.*, vol. 7, pp. 1078-1082 (1971), Gruntfest et al.
*Zh. Org. Khim.*, vol. 8, pp. 405-411 (1972), Guntfest et al.

*Primary Examiner*—C. Warren Ivy
*Assistant Examiner*—Amelia A. Owens
*Attorney, Agent, or Firm*—Woodard, Emhardt, Naughton, Moriarty & McNett

[57] ABSTRACT

Bromonitroethenylfuran (BNEF) is prepared from furfural in a two-step process. A primary amine is reacted with furfural in an organic solvent at the reflux temperature of the solvent to form the Schiff base. The organic solvent and the water formed in the foregoing reaction are removed from the Schiff base, which is then dissolved in a polar, water-miscible solvent. Bromonitromethane is added to the Schiff base solution and reacts with the Schiff base to form BNEF, which can be readily isolated by precipitation.

24 Claims, No Drawings

PROCESS FOR THE PREPARATION OF 2-(2-BROMO-2-NITROETHENYL)FURAN

REFERENCE TO RELATED APPLICATIONS

This application is a continuation in part of U.S. Pat. application Ser. No. 621,339, filed on Dec. 3, 1990 now ABN and entitled PROCESS FOR THE PREPARATION OF 2-(2-BROMO-2-NITROETHENYL)FURAN.

FIELD OF THE INVENTION

This invention relates to processes for the preparation of bromonitroethenyl furan, and particularly to a process which produces 2-(2-Bromo-2-nitroethenyl)furan (BNEF) in high purity and yield.

DESCRIPTION OF THE PRIOR ART

The use of 2-(2-Bromo-2-nitroethenyl)furan as an antimicrobial with a broad spectrum of uses in water treatment, pulp and paper manufacturing, metal working fluids and various non-oxidizing biocide applications has been described. One process for producing BNEF comprises the reaction of furfural with bromonitromethane using a primary amine or primary amine salt and sodium carbonate as the catalytic agent at 10 mol% to produce an intermediate 2-Bromo-1-(2-furyl)-2-nitroethanol, which is dehydrated in the presence of acid to the desired product. The preferred solvent is ethanol. In a typical procedure, the reaction mixture is stirred for 25 hours at 5° C., and the acid is then added to effect the dehydration. The reaction mixture is extracted with methylene chloride and the crude product recovered as an oil which is steam-distilled. The solid product is filtered from the steam-distillate and recrystallized from ethanol, and the yield is reported to be in the range of 23%.

The major disadvantages of this process are the lengthy reaction times to form the intermediate which in a further step needs to be dehydrated, the need for extensive and costly purification procedures such as steam-distillation and recrystallization, the low yield, and the use of ethanol as the solvent. The use of ethanol as an industrial solvent is surrounded by many restrictions.

Another procedure for synthesis of bromonitroethenylfuran is described by Z. N. Nazarova and G. F. Potemkin in *Khim. Farm. Zh.*, v. 6 (10), pp. 629-632 (1972), "Synthesis of Some Furylnitroolefins with Potential Biological Activity". In accordance with this method, the appropriate 5-substituted furfural is condensed with bromonitromethane in the presence of KOH catalyst. Bromonitroethenylfuran, specifically, is synthesized as follows. To furfural and bromonitromethane in methanol is added a solution of KOH in water with cooling. The reaction mixture is kept in a cooling bath for 30 minutes, and water is then added and the mixture poured into dilute HCl. After 30 minutes, the precipitate (or oil) is separated, washed with water, purified by steam-distillation and recrystallized from ethanol. Reported yield is 70.5%. Attempts to duplicate these results in our laboratory were unsuccessful, resulting largely in unworkable tars with only traces of isolatable product.

A similar procedure for synthesizing methyl-nitroethenyl-and nitroethanylfurans is reported by Gruntfest, et al. in *Zh. Org. Khim*, vol. 7, pp. 1078-1082 (1971), cited in M. G. Gruntfest, et al., *Zh. Org. Khim.*, vol. 8, pp. 405-411 (1972) "Physicochemical Properties and Reactivities of Furylnitroolefins". Equimolar quantities of furfural and nitroparaffin in methanol are treated with 2 moles of aqueous KOH. The mixture is acidified and the precipitate is filtered off, washed and dried, and recrystallized from ethanol or steam-distilled. Yield and assay for the bromonitroethenylfuran were not given.

In contrast to the prior art, the process of our invention uses inexpensive industrial solvents, requires only a three-hour hold period, does not require steam-distillation or recrystallization, and provides a 94% yield of high-assay (greater than 98%) product.

SUMMARY OF THE INVENTION

Briefly describing one aspect of the present invention, there is provided a process for preparing 2-(2-Bromo-2-nitroethenyl)furan which comprises converting furfural to a Schiff base in an organic solvent, isolating the Schiff base by removing the organic solvent therefrom, dissolving the Schiff base in a polar, water-miscible solvent, reacting the Schiff base solution with bromonitromethane, and isolating the 2-(2-Bromo-2-nitroethenyl)furan product from the reaction mixture.

It is an object of the present invention to provide an improved process for the production of 2-(2-Bromo-2-nitroethenyl)furan, a potent, broad-spectrum industrial, non-oxidizing microbiocide.

A further object is to provide a process which produces bromonitroethenylfuran in a high state of purity and eliminates the need for steam distillation and recrystallization, costly and cumbersome operations practiced in the prior art.

Further objects and advantages of the present invention will be apparent from the description which follows.

DESCRIPTION OF THE PREFERRED EMBODIMENT

For the purposes of promoting an understanding of the principles of the invention, reference will now be made to the Preferred embodiment of the invention and specific language will be used to describe the same. It will nevertheless be understood that no limitation of the scope of the invention is thereby intended, such alterations, modifications and further applications of the principles of the invention being contemplated as would normally occur to one skilled in the art to which the invention relates.

This invention is concerned with a new and superior process for producing 2-(2-Bromo-2-nitroethenyl)furan. The superiority of this process lies in the fact that the product is recovered in very high yield and assay, with a minimum of purification. In contrast, the prior art processes produced the compound in lower yields and required extensive and costly cleanup procedures.

The process of this invention broadly consists of the following steps. The furfural is converted to its imine or Schiff base in an organic solvent, followed by removal of the organic solvent and concomittant removal of the water produced in the Schiff base formation. The Schiff base is dissolved in a polar solvent and this solution is then reacted with bromonitromethane. The product is isolated by diluting the reaction mixture with water to produce the BNEF as a precipitate, followed by filtering.

Conversion of furfural to its Schiff base is effected by reacting a primary amine with furfural in an organic solvent. The amine is preferably an aliphatic amine such as n-butylamine, although aromatic amines are also suitable. Further examples of suitable amines for reaction with the furfural are $C_1$-$C_8$ primary aliphatic amines, primary arylalkylamines including benzylamine, chlorobenzylamine and methylbenzylamine, and aromatic primary amines including aniline, toluidine, p-chloroaniline and xylidene. The preferred primary amine is an aliphatic one, which may more specifically include methylamine, ethylamine, n-propylamine, i-propylamine, n-butylamine, i-butylamine, t-butylamine, n-amylamine, t-amylamine, 1-methylbutylamine and 2-methylbutylamine, of which the most preferred ones are n-butylamine, n-propylamine, ethylamine and n-amylamine. It will be appreciated that amines which are highly volatile can cause handling problems, and that amines having too high a boiling point are less desired in view of the subsequent distillation step. n-Butylamine performs well in this process.

The solvent and the water formed during conversion of the furfural is then removed from the Schiff base. The organic solvent is preferably selected from the class of solvents which will form an azeotrope with water, and the water formed in the reaction is then removed along with the organic solvent by azeotropic distillation. When the theoretical amount of water has been collected, the organic solvent is stripped off. Appropriate organic solvents can be readily selected by those skilled in the art. Examples of suitable organic solvents include cyclohexane, methylcyclohexane, methylene dichloride, ethylene dichloride, chloroform, benzene, toluene, o-xylenes, m-xylenes, p-xylenes, and aliphatic alcohols such as methyl, ethyl, n-propyl, i-propyl, n-butyl, i-butyl and t-butyl alcohols. The preferred solvents are cyclohexane, methylcyclohexane, toluene and methylene chloride.

The residual Schiff base is then dissolved in a polar, water-miscible solvent, preferably a water-miscible carboxylic acid, for reaction with bromonitromethane. Preferred water-miscible solvents include acetic acid and propionic acid. Other appropriate solvents may be readily selected by one skilled in the art given the desired aspects described herein for such solvent. The use of a water-miscible solvent permits a simple product isolation procedure involving quenching with water to precipitate the product in high yield and assay, followed by purification by a simple aqueous wash. On the other hand, the use of a water-immiscible organic solvent would require stripping this solvent and recovery of a bottoms product contaminated with undesirable by-products and therefore requiring extensive purification procedures.

The Schiff base solution is then reacted with bromonitromethane to form a reaction mixture including 2-(2-Bromo-2-nitroethenyl)furan. BNEF forms as a precipitate from the reaction mixture during the hold period. Diluting the reaction mixture with water precipitates the remainder of the product. The product may then be isolated by conventional methods.

The following examples, tabulated below, demonstrate the improvements achieved by the present invention process and, in particular, the advantages of forming the Schiff base intermediate in providing high yield and assay of bromonitroethenylfuran. It will be understood that these Examples are illustrative and not restrictive in nature.

EXAMPLE 1

Using 10 mol% butylamine in methanol, analogous to the use of 10 mol% $CH_3NH_2HCl/Na_2CO_3$ in the prior art process, bromonitromethane was reacted with furfural and butylamine without prior formation of the Schiff base. After several hours of stirring, under various conditions, the product was isolated and determined to have been produced in low yields.

EXAMPLE 2

This example as set forth in Table I demonstrates that using acetic acid as the solvent, rather than methanol, with catalytic amounts of amine, without prior formation of the Schiff base, affords high-assay product but in very low yield.

EXAMPLE 3

This example demonstrates that even when a stoichiometric amount of butylamine is used, unless the Schiff base is formed first and isolated by removing the solvent and the water formed, the product is recovered as a tar. Stoichiometric quantities of furfural and butylamine were charged to methanol at 5–10° C. in a nitrogen atmosphere. After 20 minutes, bromonitromethane was added at 5° C. The reaction mixture was stirred at from 2° C. to 28° C. for 3 hours, then stored in the refrigerator. Upon quenching in water at 0–5° C., a black tar was recovered.

EXAMPLE 4

In this example, the Schiff base was formed in methanol, but in contrast to Example 3, the methanol was stripped off and replaced with acetic acid, followed by addition of bromonitromethane in accordance with the present invention. Good yields and high assay product were obtained.

Stoichiometric quantities of furfural and butylamine were charged to methanol at 20–25° C. under a nitrogen atmosphere. After 50 minutes of stirring at 23° C. an additional 5 mol% of butylamine was added. However, this had no notable effect on the NMR profile. After holding overnight at ambient temperature, the methanol and water were stripped off. The residual Schiff base was dissolved in acetic acid at 0° C., and bromonitromethane was then added at the same temperature. After 2 hours of stirring at 26° C. the reaction slurry was quenched in water, and the product was filtered, washed and dried. A yield of 89.4% of product was obtained, assaying 96.5%.

EXAMPLE 5

This example further demonstrates the process of this invention. Furfural (1009.1 g; 10.5 mols) and 1000 ml of cyclohexane were charged to a 5 liter, 5-neck round-bottom flask. n-Butylamine, 768.0 g (10.5 mols), was added from a dropping funnel in 50 minutes, keeping the temperature below 60° C. The mixture was then heated at reflux for 4 hours, at which time the theoretical quantity of water had distilled over. The solution was then stripped at reduced pressure. The Schiff base intermediate was recovered as a bottoms product in 98.7 % yield (1567.5 g), assaying 99.4% by GC, and was used in the subsequent condensation without further purification.

The Schiff base, 756.0 g (5.0 mols), was charged to a well-stirred, 5 liter, 5-neck round-bottom flask. Acetic acid (1250 ml) was added in one-half hour at 15° C. to 20° C. This was followed by the addition of 727.9 g (5.0 mols, 96.1% assay) of bromonitromethane at 15° C. to 20° C. Upon completion of this addition, stirring was continued for three hours at 20–25° C. The product precipitated during the first 20 minutes of this hold period. The product slurry was then quenched with 2500 ml of ice-cold water. The product was filtered, washed successively with water, 0.5% sodium bicarbonate solution, and finally with two more water washes, and dried under vacuum. This procedure produced 1037.1 g of 2-(2-Bromo-2-nitroethenyl)furan (95.1% yield), assaying 99.4% by GC.

TABLE I 2-(2-Bromo-2-Nitroethenyl) Furan (BNEF)

| Ex. No. | BuNH$_2$ | Schiff Base formed prior to Bromonitromethane Addition | Solvent for Condensation | BNEF Yield, % | Assay % |
|---|---|---|---|---|---|
| 1 | 10 mol % | No | MeOH | 25–39 | 89.0 |
| 2 | 10 mol % | No | HOAc | 66.3 | 98.4 |
| 3 | Stoich. | No | MeOH | Tar | |
| 4 | Stoich. | Yes | HOAc | 89.4 | 96.5 |
| 5 | Stoich. | Yes | HOAc | 93.9 | 99.4 |

What is claimed is:

1. A process for preparing 2-(2-bromo-2-nitroethenyl) furan which comprises the steps of:
   a. converting furfural to a Schiff base in an organic solvent, said converting comprising reacting the furfural with a primary amine, said reacting yielding the Schiff base and water;
   b. isolating the Schiff base by removing the organic solvent and the water from the Schiff base;
   c. dissolving the Schiff base in a polar, water-miscible solvent;
   d. reacting the Schiff base solution of step c with bromonitromethane to form a reaction mixture including 2-(2-bromo-2-nitroethenyl)furan; and
   e. isolating the 2-(2-bromo-2-nitroethenyl) furan product from the reaction mixture.

2. The process of claim 1 in which the primary amine is a primary aliphatic amine.

3. The process of claim 2 in which the primary amine is n-butylamine.

4. The process of claim 2 in which step c comprises dissolving the Schiff base in acetic acid.

5. The process of claim 1 in which the organic solvent forms an azeotrope with water, and in which step b comprises removal of the organic solvent and water by azeotropic distillation.

6. The process of claim 5 in which step c comprises dissolving the Schiff base in acetic acid.

7. The process of claim 6 in which the primary amine is n-butylamine.

8. The process of claim 7 in which step e comprises quenching the reaction mixture of step d with water to precipitate the 2-(2-Bromo-2-nitroethenyl) furan product.

9. The process of claim 1 in which the organic solvent of step a. is selected from the group consisting of cyclohexane, methylcyclohexane, methlyene dichloride, ethylene dichloride, chloroform, benzene, toluene, o-xylene, m-xylene, p-xylene, and aliphatic alcohols selected from methyl, ethyl, n-propyl, i-propyl, n-butyl, i-butyl and t-butyl alcohols.

10. The process of claim 9 in which the organic solvent is selected from the group consisting of cyclohexane, methylcyclohexane, toluene, methylene dichloride and methanol.

11. The process of claim 9 in which the organic solvent of step a. is methanol.

12. The process of claim 1 in which the polar, water-miscible solvent of step c. is a carboxylic acid.

13. The process of claim 12 in which the polar, water-miscible solvent is selected from the group consisting of acetic acid and propionic acid.

14. The process of claim 13 in which the polar, water-miscible solvent is acetic acid.

15. The process of claim 1 in which the primary amine of step a. is selected from the group consisting of aliphatic primary amines and aromatic primary amines.

16. The process of claim 15 in which the primary amine of step a. is selected from the group consisting of $C_1$–$C_8$ primary aliphatic amines, primary arylalkylamines and aromatic primary amines.

17. The process of claim 16 in which the primary amine is a primary aliphatic amine selected from the group consisting of methylamine, ethylamine, n-propylamine, i-propylamine, n-butylamine, i-butylamine, t-butylamine, n-amylamine, t-amylamine, 1-methylbutylamine and 2-methylbutylamine.

18. The process of claim 17 in which the primary amine is selected from the group consisting of ethylamine, n-propylamine, n-butylamine and n-amylamine.

19. The process of claim 18 in which the primary amine is n-butylamine.

20. The process of claim 16 in which the primary amine is a primary arylalkylamine selected from the group consisting of benzylamine, chlorobenzylamine and methylbenzylamine.

21. The process of claim 16 in which the primary amine is an aromatic primary amine selected from the group consisting of aniline, toluidine, p-chloroaniline and xylidene.

22. The process of claim 16 in which the primary amine is selected from the group consisting of methylamine, ethylamine, n-propylamine, i-propylamine, n-butylamine, i-butylamine, t-butylamine, n-amylamine, t-amylamine, 2-methylbutylamine, 2-methylbutylamine, benzylamine, chlorobenzylamine, methylbenzylamine, aniline, toluidine, p-chloroaniline and xylidene.

23. The process of claim 1 in which:
   the organic solvent of step a. is selected from the group consisting of cyclohexane, methylcyclohexane, methylene dichloride, ethylene dichloride, chloroform, benzene, toluene, o-xylene, m-xylene, p-xylene, and aliphatic alcohols selected from methyl, ethyl, n-propyl, i-propyl, n-butyl, i-butyl and t-butyl alcohols;
   the polar, water-miscible solvent is selected from the group consisting of acetic acid and propionic acid; and
   the primary amine is selected from the group consisting of methylamine, ethylamine, n-propylamine, i-propylamine, n-butylamine, i-butylamine, t-butylamine, n-amylamine, t-amylamine, 2-methylbutylamine, 2-methylbutylamine, benzylamine, chlorobenzylamine, methylbenzylamineaniline, toluidine, p-chloroaniline and xylidene.

24. The process of claim 23 in which the organic solvent is methanol, the polar, water-miscible solvent is acetic acid, and the primary amine is n-butylamine.

* * * * *

UNITED STATES PATENT AND TRADEMARK OFFICE
CERTIFICATE OF CORRECTION

PATENT NO. : 5,138,076

DATED : August 11, 1992

INVENTOR(S) : Fred R. Gerns, Larry D. Timberlake

It is certified that error appears in the above-identified patent and that said Letters Patent is hereby corrected as shown below:

In Column 2, line 43 change "Preferred" to --preferred--.

In Column 6, line 43 change "2-methylbutylamine" to --1-methylbutylamine--.

In Column 6, line 60 change "2-methyl" to --1-methyl--.

Signed and Sealed this

Twenty-fourth Day of August, 1993

Attest:

BRUCE LEHMAN

*Attesting Officer*        *Commissioner of Patents and Trademarks*